(12) United States Patent
Farag

(10) Patent No.: US 9,017,393 B2
(45) Date of Patent: Apr. 28, 2015

(54) RELEASABLE TOP CAP ASSEMBLY

(71) Applicant: Cook Medical Technologies LLC, Bloomington, IN (US)

(72) Inventor: Jacqueline Farag, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/658,912

(22) Filed: Oct. 24, 2012

(65) Prior Publication Data

US 2013/0110041 A1    May 2, 2013

Related U.S. Application Data

(60) Provisional application No. 61/553,787, filed on Oct. 31, 2011.

(51) Int. Cl.
| | |
|---|---|
| *A61F 2/06* | (2013.01) |
| *A61F 2/966* | (2013.01) |
| *A61F 2/95* | (2013.01) |
| *A61F 2/962* | (2013.01) |
| *A61F 2/07* | (2013.01) |
| *A61F 2/82* | (2013.01) |

(52) U.S. Cl.
CPC .......... *A61F 2/966* (2013.01); *A61F 2002/9511* (2013.01); *A61F 2/962* (2013.01); *A61F 2/07* (2013.01); *A61F 2/82* (2013.01); *A61F 2/95* (2013.01); *A61F 2002/9505* (2013.01); *A61F 2002/9665* (2013.01)

(58) Field of Classification Search
CPC ........... A61F 2/95; A61F 2/962; A61F 2/966; A61F 2002/9665; A61F 2002/9511

USPC ................................ 623/1.11–1.12; 606/108
See application file for complete search history.

(56) References Cited

U.S. PATENT DOCUMENTS

| | | | | |
|---|---|---|---|---|
| 5,480,423 | A * | 1/1996 | Ravenscroft et al. | 623/1.11 |
| 2003/0233140 | A1* | 12/2003 | Hartley et al. | 623/1.11 |
| 2005/0143770 | A1 | 6/2005 | Carter et al. | |
| 2010/0211156 | A1 | 8/2010 | Linder et al. | |
| 2011/0054587 | A1* | 3/2011 | Mayberry et al. | 623/1.11 |

FOREIGN PATENT DOCUMENTS

WO    WO 2011/066847    6/2011

OTHER PUBLICATIONS

European Search Report, EP 12275167, search completed Jan. 28, 2013.

* cited by examiner

*Primary Examiner* — Theodore Stigell
*Assistant Examiner* — Benjamin Koo
(74) *Attorney, Agent, or Firm* — Brinks Gilson & Lione

(57) ABSTRACT

A releasable top cap system for a delivery device having an emergency release includes a top cap having a top portion and a bottom portion releasably attached to the top portion, the bottom portion having two adjacent side portions. A cannula is positioned distal to the top cap having a proximal end and a distal end. A connector is attached to the proximal end of the cannula. A pair of wire components extend throughout the length of the cannula. Each wire component has a distal end and a proximal end. The proximal end of each wire component is attached to the male luer lock component and the distal end of each wire component is attached to the side portions of the top cap assembly.

20 Claims, 4 Drawing Sheets

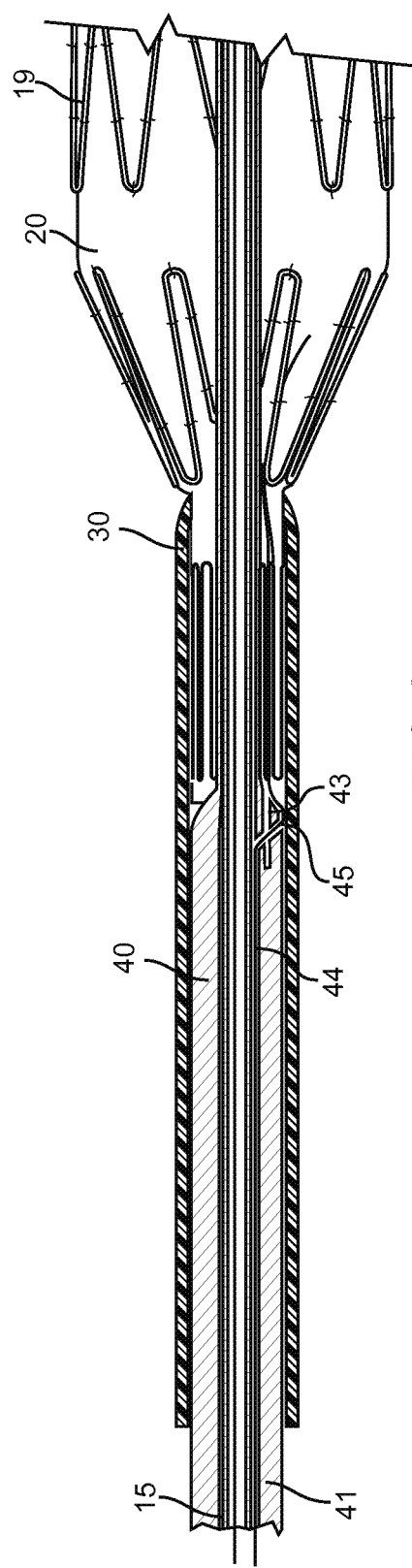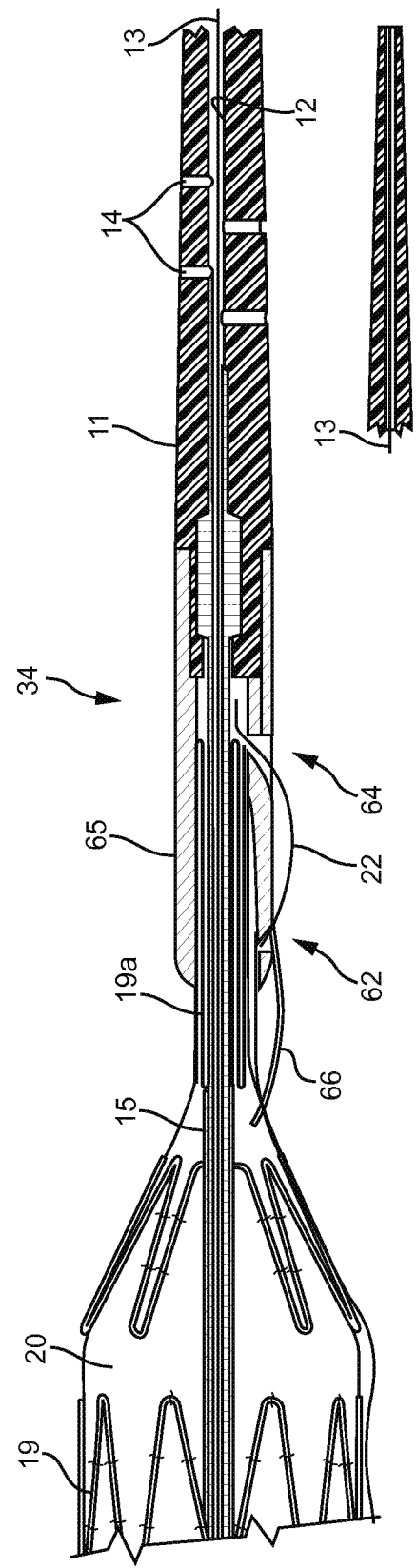

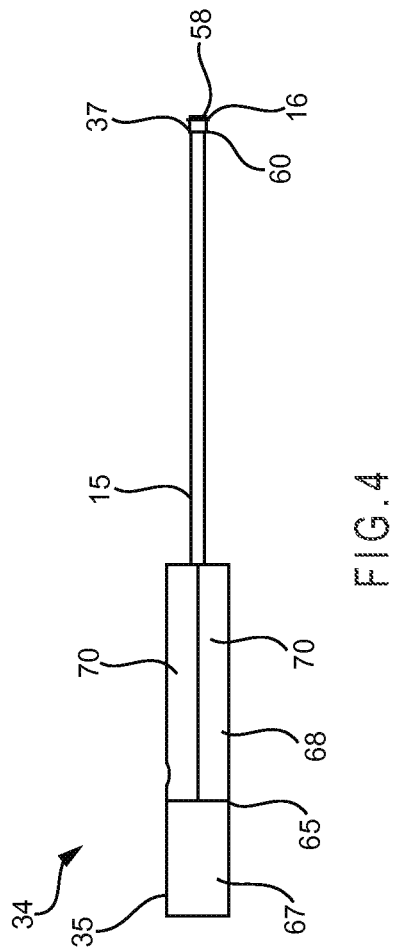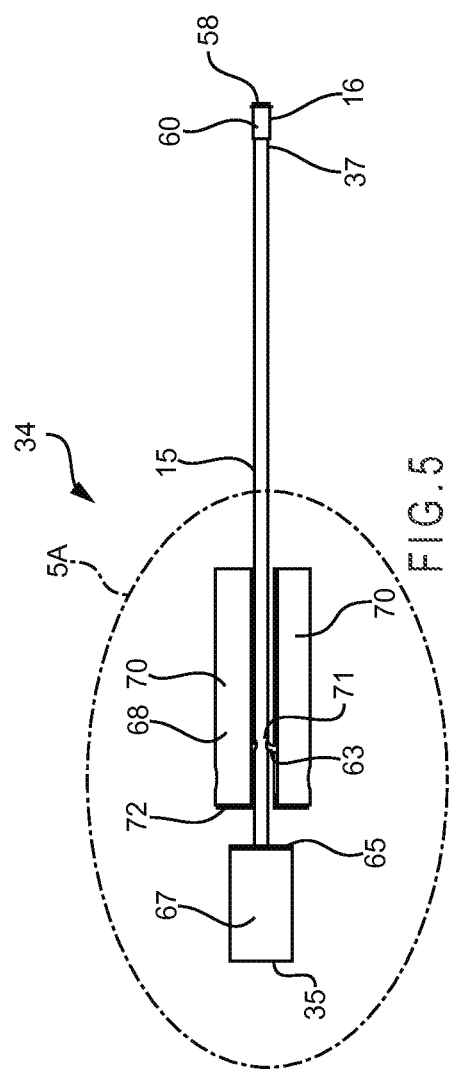

RELEASABLE TOP CAP ASSEMBLY

The present application claims priority to U.S. Provisional Patent Application Ser. No. 61/553,787 filed Oct. 31, 2011, the entirety of which is hereby incorporated by reference.

TECHNICAL FIELD

The present invention relates to medical devices, and particularly, to a delivery system for delivering a medical device to a selected site.

BACKGROUND

The physiological passageways and cavities of human and animal bodies, for example, blood vessels and ducts, occasionally weaken or even rupture. One common surgical intervention for weakened, aneurysmal or ruptured passageways or ducts involves the use of an endoluminal prosthesis to provide some or all of the functionality of the original, healthy passageway or duct and/or preserve any remaining vascular integrity by replacing a length of the existing passageway or duct wall that spans the site of failure or defect. Endoluminal prostheses may be of a unitary construction or may be comprised of multiple prosthetic modules.

Delivery catheters or sheaths are widely used for the delivery of a stent or a stent graft to a deployment site well within the vasculature of the patient. Typically, the delivery catheter is inserted over a guide wire. In one common arrangement, used particularly with self-expanding stents, an inner core carries the stent and has a distal tip that is atraumatic and may assist in dilating the vessel as the delivery catheter advances along the guide wire. A sheath covers the stent during the delivery procedure and maintains or assists in maintaining the stent in its radially compressed configuration. The distal tip will usually have a smooth outer surface, tapering axially from a relatively large outer diameter, corresponding to the outside diameter of the sheath, to a relatively small outer diameter at the distal end of the sheath, corresponding (with an appropriate wall thickness for the tip) to the outside diameter of the wire guide. Once the stent has reached the deployment site, the sheath is withdrawn, uncovering the stent and allowing it to expand radially.

When endoluminal prostheses or antistenotic stents are implanted to treat these or similar conditions, it is important that they do not migrate under physiological forces. Pulsatile flow is a major force that stents encounter, thus stents and endoluminal prostheses tend to move downstream in the blood vessel. If the stents or endoluminal prosthesis migrate, they can travel beyond the length of the vessel they are intended to treat. For example, if an antistenotic stent migrates, it will fail to keep the targeted portion of the vessel from restenosing. Accordingly, the endoluminal prosthesis may include an attachment stent disposed on an end portion thereof. The attachment stent may comprise a plurality of barbs that in use are adapted to anchor the prosthesis to a surrounding body lumen. An end portion of the attachment stent is retained within the delivery device by a cover, or a top cap, in order to keep the attachment stent in a radially constrained state. To deploy the prosthesis, the operator withdraws the top cap from the attachment stent, thereby exposing the stent and allowing it to expand radially outwardly.

The stent radially expands against an inner surface of the top cap prior to deployment. The expansion force of the stent against the inner surface can be sufficiently high so as to create significant interference between the stent and the top cap. This can result in increased operating effort to remove the cover from the stent. This is particularly true where the stent comprises sharpened barbs that may scratch or dig into the inner surface of the top cap.

BRIEF SUMMARY

In one aspect, a releasable top cap assembly for a delivery device having an emergency release includes a top cap having a top portion and a bottom portion releasably attached to the top portion, the bottom portion having two adjacent side portions. A cannula is disposed through the top cap having a proximal end and a distal end. A connector is attached to the proximal end of the cannula. A pair of wire components extend throughout the length of the cannula. Each wire component has a distal end and a proximal end. The proximal end of each wire component is attached to the connector and the distal end of each wire component is attached to the side portions of the top cap assembly. In some aspects, the connector of the releasable top cap assembly comprises a cooperating male luer lock component and a female luer lock component. In other aspects, the distal ends of the pair of wire components are curved outward from the outer surface of the cannula.

In another aspect, delivery device for an endoluminal prosthesis includes a dilator having a distal end and a proximal end. A releasable top cap assembly is positioned distal to the dilator. The releasable top cap assembly comprises a top cap having a top portion and a bottom portion releasably attached to the top portion, the bottom portion having two adjacent side portions. A cannula is disposed through the top cap having a proximal end and a distal end. A connector is attached to the proximal end of the cannula. A pair of wire components extend throughout the length of the cannula. Each wire component has a distal end and a proximal end. The proximal end of each wire component is attached to the connector and the distal end of each wire component is attached to the side portions of the top cap assembly. In some aspects, the cannula includes at least two apertures on opposing sides of the outer surface of the cannula. In other aspects, the connecter includes a male luer lock component and a female luer lock component and a male luer lock component of the connector, where the male luer lock component is moved proximally to remove the two side portions of the top cap.

In yet another aspect, a system for endoluminally delivering and deploying an endoluminal prosthesis includes a prosthesis having an end portion and a body portion, the end portion including a stent. The system further includes a releasable top cap assembly for maintaining at least a portion of the stent until deployment, the releasable top cap assembly comprising a top cap having a top portion and male luer lock component. A cannula is disposed through the top cap having a proximal end and a distal end. A connector is attached to the proximal end of the cannula. A pair of wire components extends throughout the length of the cannula. Each wire component has a distal end and a proximal end. The distal end of each wire component is bowed outwardly in the direction of the side portions of the top cap. The two side portions of the top cap are released upon movement of the locking mechanism.

BRIEF DESCRIPTION OF THE DRAWINGS

FIG. 2 is a sectional detail view of a portion of a delivery device of FIG. 1 around the proximal end of the prosthesis.

FIG. 3 is a sectional detail view of a portion of the delivery device of FIG. 1 around the distal end of the prosthesis.

FIG. 4 is a side view of an embodiment of the releasable top cap assembly of the delivery device of FIG. 1 in a closed position.

DETAILED DESCRIPTION OF THE DRAWINGS AND THE PRESENTLY PREFERRED EMBODIMENTS

Figure 1:
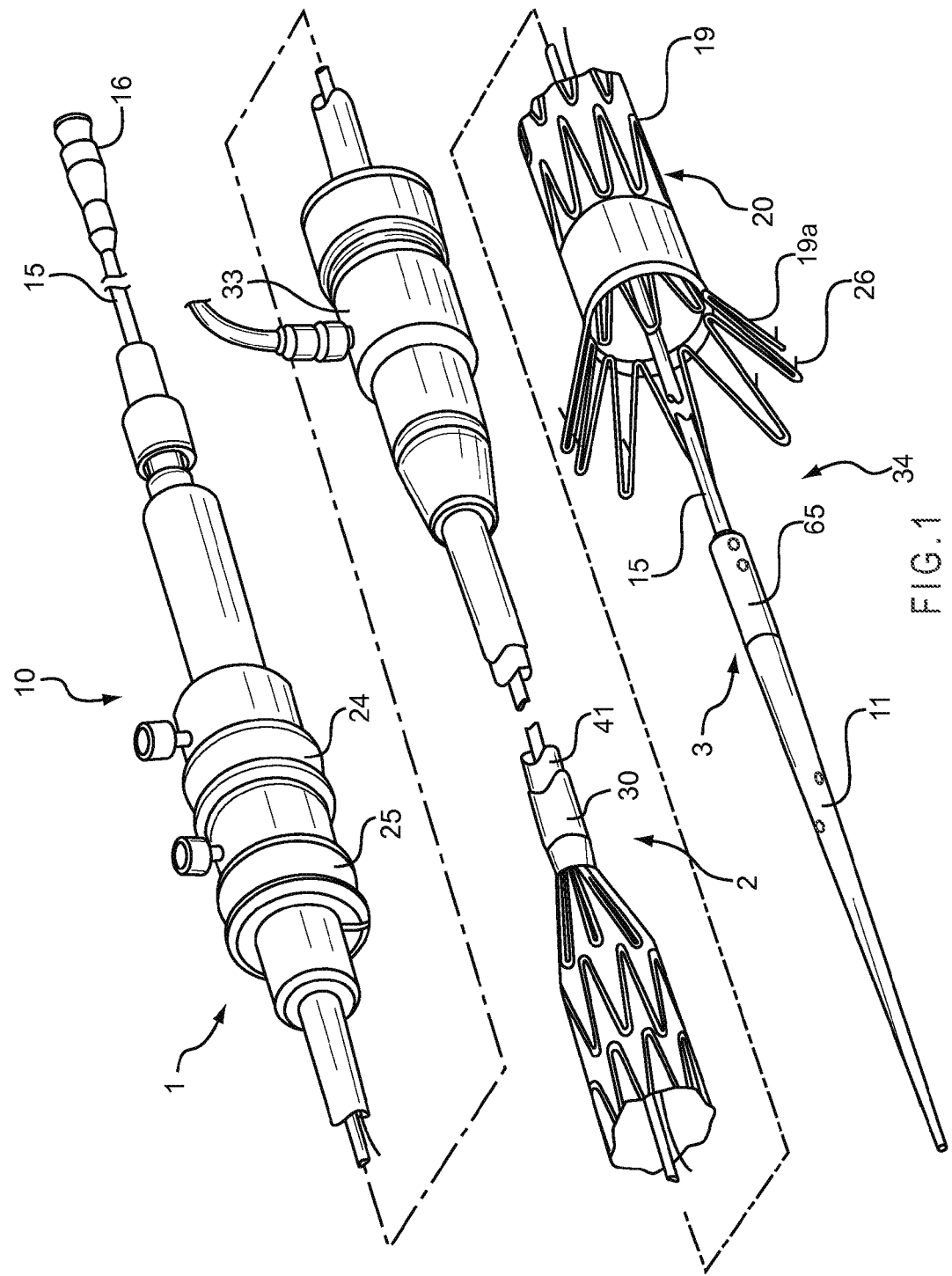
FIG. 1 is a perspective view of an aspect of the delivery device with a releasable top cap assembly.

Unless defined otherwise, all technical and scientific terms used herein have the same meaning as commonly understood to one of ordinary skill in the art to which this invention belongs.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "endoluminal" refers to or describes the internal or inside of a lumen, duct, and other passageways or cavities located in a human or other animal body. A lumen or a body passageway may be an existing lumen or a lumen created by surgical intervention. As used in this specification, the terms "lumen" or "body passageway," and "vessel" are intended to have a broad meaning and encompass any duct (e.g., natural or iatrogenic) or cavity within the human body and may include without limitation, blood vessels, respiratory ducts, gastrointestinal ducts, such as the biliary duct, intestines, the esophagus, the pericardial cavity, the thoracic cavity, the pericardial cavity, and the like. Accordingly, the terms "endoluminal device" or "endoluminal prosthesis" describe devices that can be placed inside or moved through any such lumen or duct.

The term "graft" or "graft material" describes an object, device, or structure that is joined to or that is capable of being joined to or implanted in or against a body part to enhance, repair, or replace a portion or a function of that body part. A graft by itself or with the addition of other elements, such as structural components, may comprise an endoluminal prosthesis. The graft may be comprised of a single material, a blend of materials, a weave, a laminate, or a composite of two or more materials. The graft may also be constructed from a synthetic, for example and without limitation, a polymer. The graft may be formed from a single layer or multiple layers of material. In embodiments employing a plurality of layers of material, the layers may remain separate, or may be attached to each other through a secondary process such as sintering, curing, adhesives, and sutures or the like.

The terms "patient," "subject," and "recipient" as used in this application may refer to any animal, particularly humans.

The terms "proximal" and "distal" will be used to describe opposing axial ends of the delivery system, as well as the axial ends of various component features. The term "distal" is used to refer to the end of the system (or component thereof) that is initially inserted into the patient, or that is closest to the patient during use. The term "proximal" is used to refer to the end of the system (or component thereof) that is closest to the physician during use of the system.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "about" used with reference to a quantity includes variations in the recited quantity that are equivalent to the quantity recited, such as an amount that is insubstantially different from a recited quantity for an intended purpose or function.

FIG. 1 shows an endovascular delivery device 10 which can be used for delivering and deploying an endoluminal prosthesis 20, such as a stent graft, in a lumen of a patient. The delivery device 10 includes an external manipulation section 1, a proximal positioning mechanism or attachment region 2, and a distal positioning mechanism or attachment region 3. During a medical procedure to deploy the endoluminal prosthesis 20, the proximal and distal attachment regions 2 and 3 will travel through a desired deployment site. The external manipulation section 1, which is acted upon by a user to manipulate the delivery device 10, remains outside of the patient throughout the procedure.

The endoluminal prosthesis 20 is preferably made from biocompatible material. Preferably the biocompatible material is in the form of a fabric that is impermeable to liquids, including blood or other physiological fluids. Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. For example, the endoluminal prosthesis 20 may be constructed from woven multifilament polyester, for example and without limitation, Dacron™, produced by DuPont. Dacron™ is known to be sufficiently biologically inert, non-biodegradable, and durable to permit safe insertion inside the human body. The endoluminal prosthesis 20 may also include a plurality of self-expanding stents 19 that are attached along the length of the endoluminal prosthesis 20. The endoluminal prosthesis 20 includes a self-expanding stent 19a that is attached to the proximal end of the endoluminal prosthesis 20. The self-expanding stent 19a may be a bare wire stent and may include barbs 26 that extend from the stent 19a distal end. When the self-expanding stent 19a is released, the barbs 26 anchor the distal end of the endoluminal prosthesis 20 to the surrounding lumen (not shown).

The stents 19, 19a may be made from numerous metals and alloys. In one example, the stents 19, 19a comprise a shape-memory material such as a nickel-titanium alloy ("Nitinol"). Moreover, the structure of the stents 19, 19a may be formed in a variety of ways to provide a suitable support structure. For example, one or more stents may be made from a woven wire structure, a laser-cut cannula, individual interconnected rings, or another pattern or design. While one exemplary arrangement is shown in FIG. 1, it will be appreciated that the exact number of stents, and their location, may be varied.

These stents may be configured in the form of "Z-stents", each of which may comprise a series of substantially straight segments interconnected by a series of bent segments. The bent segments may comprise acute bends or apices. The Z-stents are arranged in a zigzag configuration in which the straight segments are set at angles relative to each other and are connected by a bent segment. However, as noted above, the stents 19, 19a may comprise any suitable configuration and one or more stents may be provided. The self-expanding stents 19, 19a cause the endoluminal prosthesis 20 to expand when released from the delivery device 10. The self-expanding stents 19, 19a may be disposed on the interior surface of the endoluminal prosthesis 20. Alternatively, the stents 19, 19a may be disposed on the exterior surface of the endoluminal prosthesis 20.

A sheath 30 retains the endoluminal prosthesis 20 in a compressed condition on the delivery device 10. The sheath 30 comprises a generally elongate tubular body. The endoluminal prosthesis 20 is disposed within the sheath lumen. The endoluminal prosthesis 20 and the self-expanding stents 19 radially expand against the inner surface of the sheath 30. The sheath 30 preferably comprises a flexible material so that in use it is able to negotiate tortuous vasculature of the patient. The sheath 30 may also comprise a lubricious or slippery material to facilitate insertion and withdrawal of a tube 41 and of catheters and the like therethrough. Accordingly, the sheath 30 may comprise a plastic material, such as polytetrafluoroethylene (PTFE), polyethylene, nylon, or the like.

The sheath 30 radially compresses the endoluminal prosthesis 20 over a distal portion of a thin cannula 15. The cannula 15 is generally flexible and may be made of metal, for example stainless steel or Nitinol. A connector 16 is positioned proximal of the cannula 15. A tube 41, which can be made of plastic, is coaxial with and radially outside the cannula 15. The distal end of the tube 41 is adjacent the proximal end of the endoluminal prosthesis 20. The tube 41 is "thick walled", which is to say the thickness of the wall of tube 41 is several times that of the cannula 15. Preferably, the tube 41 is five or more times thicker than the cannula 15. The sheath 30 is coaxial with and radially outside the thick walled tube 41. The thick walled tube 41 and the sheath 30 extend proximally to the manipulation region 1. The cannula 15 extends proximally to the proximal end of the delivery device 10. The delivery device 10 further includes homeostatic sealing means 33 radially disposed about the sheath and the thick walled tube. The homeostatic sealing means 33 controls the loss of blood through the delivery device 10 during a procedure. FIG. 1 also shows a top cap 65 of a releasable top cap assembly 34 configured to retain stent 19a. Positioned distal to the top cap assembly 65 is a long tapered flexible dilator 11. A distal release wire mechanism 24 is provided to control a trigger wire to retain a distal end of the endoluminal prosthesis 20. A proximal release wire mechanism 25 is provided to control a trigger wire to retain a proximal end of the endoluminal prosthesis 20. As will be discussed below, the top cap 65, cannula 15, and connector 16 are components of a releasable top cap assembly 34.

FIG. 2 illustrates a proximal prosthesis retention and release mechanism. The proximal retention section 40 radially and axially retains a proximal end of the endoluminal prosthesis 20 during the procedure. The proximal retention section 40 may comprise a separate body coupled to the thick walled tube 41. The proximal end of the endoluminal prosthesis 20 comprises an aperture defining a loop 43. A proximal trigger wire extends through the loop 43. A proximal trigger wire 44 extends through the loop 43 and through an aperture 45 in the proximal attachment section 40 into an annular region between the cannula 15 and the thick walled tube 41. The proximal trigger wire 44 extends proximally through the delivery device 10 from the proximal retention section 40 to the release wire actuation section located in the external manipulation section 1. Trigger wire 44 couples the proximal end of the endoluminal prosthesis 20 to the proximal retention section 40 during deployment to limit axial and radial displacement of the prosthesis. The endoluminal prosthesis 20 can be selectively released into the body lumen by disengaging the trigger wire 44 from the loop 43.

FIG. 3 illustrates a distal portion of the delivery device 10. As shown, the top cap 65 of the releasable top cap assembly 34 radially and axially retrains the distal end of the self-expanding Z-stent 19a during a procedure. Suture loops 66 and a distal trigger wire 22 for coupling the stent 19a to top cap 65 are configured to prevent inadvertent early deployment. The dilator 11 comprises an internal longitudinal aperture 12. The longitudinal aperture 12 facilitates advancement of the tapered dilator 11 along a previously inserted insertion wire 13. The longitudinal aperture 12 also provides a channel for the introduction of medical reagents. For example, it may be desirable to supply a contrast agent to allow angiography to be performed during placement and deployment phases of the medical procedure. The distal end of the cannula 15 is coupled to the dilator 11. The cannula 15 is flexible so that the delivery device 10 can be advanced within a relatively tortuous vessel, such as a femoral artery. The cannula 15 extends proximally through the delivery device 10 to the manipulation section 1, terminating at a connector 16. The cannula 15 is in mechanical communication with the dilator 11. The cannula 15 is in fluid communication with the aperture 12 of the dilator 11. Therefore, reagents introduced into connector 16 may pass through aperture 12 and can emanate from lateral apertures 14 into the body lumen. The top cap 65 of the releasable top cap assembly 34 includes apertures 62 and 64 to accommodate the distal trigger wire 22. The suture loops 66 are coupled to the body of the endoluminal prosthesis 20, and hold the self-expanding Z-stent 19a in the top cap 65 of the releasable top cap assembly 34 until the trigger wire 22 is removed. While the trigger wire 22 is in place, the suture loops 66 prevent the top cap 65 of the releasable top cap assembly 34 and the endoluminal prosthesis 20 from separating. The trigger wire 22 retains the suture loops 66 against an outer surface of the top cap 65 of the releasable top cap assembly 34. The distal trigger wire 22 extends proximally through the delivery device 10 to a release wire actuation section located in the manipulation section 1.

The suture loops 66 are attached to opposing sides of the endoluminal prosthesis 20, for example separated by 90 to 180 degrees. The suture loops 66 are generally inelastic and do not stretch. Since the suture loops 66 do not stretch, they provide opposing torques, thereby preventing the endoluminal prosthesis 20 from rotating within the top cap 65 of the releasable top cap assembly 34. This configuration differs from delivery devices that have a single point of attachment. Such devices may allow the stent to rotate within the retention device and lead to entanglement of the stent's struts. When the trigger wire 22 is removed the suture loops 66 are free to move. The top cap 65 of the releasable top cap assembly 34 may then be released from the self-expanding Z-stent 19a by sliding the top cap 65 of the releasable top cap assembly 34 distally away from the prosthesis.

FIG. 4 shows an embodiment of the releasable top cap assembly 34 in detail. As shown, the top cap assembly 34 is in the closed position prior to deployment. The top cap release assembly 34 includes a distal end 35 and a proximal end 37. Cannula 15 is configured to extend from the distal end 35 to the proximal end 37. As discussed above, the cannula 15 is disposed through the top cap 65 and extends to a dilator (not shown). The distal end 35 of the top cap assembly 34 includes a top cap 65 having at least two parts: a top portion 67 and a bottom portion 68. The bottom portion 68 of the top cap assembly 34 may comprise two abutting side portions 70 that are releasably attached to the top portion 67 of the top cap 65. The top cap 65 may be slidably moved independent from the rest of the delivery device 10 by the physician. The top cap 65 may comprise any suitable biocompatible material. For example, the top cap 65 may comprise plastic, such as PTFE, polyethylene, nylon, or the like. The top cap assembly 34 further includes the connector 16 attached to the proximal end of the cannula 15. The connector 16 may be a luer lock assembly having a male luer lock connection 58 and a female luer lock connection 60. The male luer lock connection 58 may include a needle point edge for the connection of the luer lock assembly 52 to syringes and other medical apparatus.

Figure 5A:
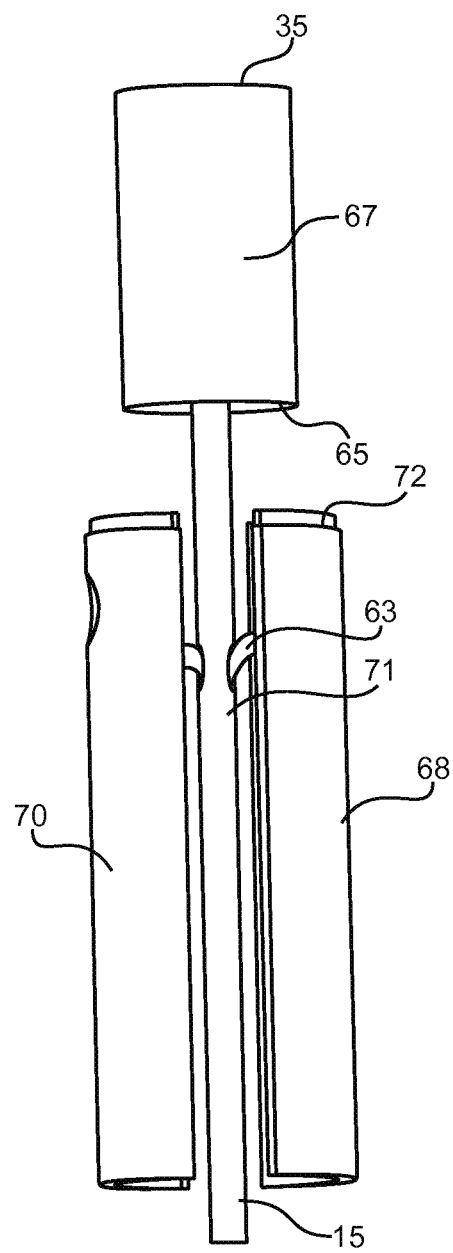
FIG. 5 is a side view of an embodiment of the releasable top cap assembly of the delivery device of FIG. 1 in a released position.

In FIG. 5, the top cap assembly 34 is shown in the released position. Each side portion 70 includes a notch 72 that is designed to engage within a retaining edge of the top portion 67 of the top cap 65 when the releasable top cap assembly 34 is in the closed position. In other embodiments, the top portion 67 of the top cap 65 may include a designated track for receiving portions of the side portions 70. A pair of wire components 63 is engaged with each side portion 70 of the bottom portion 68 of the top cap 65. Each of the components 63 is positioned on opposite sides of the cannula 15 and has a proximal end and a distal end. The wire components 63 are configured to extend axially throughout the length of the interior lumen of the cannula 15. The diameter of each wire component 63 may range from about 0.009 cm to about 0.011 cm, preferably about 0.010 cm. The proximal end of each wire component 63 is attached to the male luer lock connection 58. The proximal ends of the wire components 63 may be attached to the male luer lock connection 58 through the use of adhesives or other means. The wire components 63 may be formed from a suitable biocompatible material including, but not limited to, stainless steel and Nitinol. The distal ends of the wire components 63 exit the interior lumen of the cannula 15 through openings 71 at the distal end of the cannula 15 and bow outward to engage to side portions 70. As shown in further detail in FIG. 5A, the openings 71 are sized to accommodate the diameter of the wire components 63. The two openings 71 may be created by conventional means, such as by laser cutting.

During the endovascular procedure deploying the endoluminal prosthesis 20 within a patient, a small incision is made into the patient's skin above the femoral artery. The physician guides a guide wire into the femoral artery and advances the guide wire through the tortuous vasculature to the aneurysm. The endoluminal prosthesis 20 would be loaded into the delivery device 10. The delivery device 10 is inserted over the guide wire and inserted into the femoral artery to advance the endoluminal prosthesis 20 to the site of the aneurysm. Once the delivery device 10 is in a desired position for deployment of the endoluminal prosthesis 20, the sheath 30 can be withdrawn to just distal of the proximal attachment section 40. This action exposes the middle portion of the endoluminal prosthesis 20 so that the middle portion can expand radially outward. The self-expanding stent 19a, however, is still retained within the top cap 65 of the top cap assembly 34. The endoluminal prosthesis 20 is then positioned at or near the aneurysm. Once satisfied with the position of the endoluminal prosthesis 20, the physician may withdraw the sheath 30 of the delivery device 10 and release the endoluminal prosthesis 20 into the aorta. Once the endoluminal prosthesis 20 is in the desired position, the physician can anchor the endoluminal prosthesis 20 at a desired location with the self-expanding Z-stent 19a. The physician removes the distal trigger wire 22, which allows the top cap 65 of the top cap assembly 34 to be separated from the self-expanding Z-stent 19a, as explained above. Following the release of the one or more locking trigger wires, the top cap 65 may be slidably advanced to deploy the suprarenal stent 21. If deployment of the self-expanding Z-stent 19a is successful, the physician would remove the delivery device 10 while keeping the releasable top cap assembly 34 in the closed position.

If the self-expanding Z-stent 19a becomes entrapped in the top cap 65 of the top cap assembly 34, the physician may provide an emergency release for the self-expanding Z-stent 19a by moving the top cap assembly 34 from the closed position to the released position. The physician controls the releasable top cap assembly 34 through the use of the connector 16 of the delivery system 30. In order to position the top cap assembly 34 into the released position, the physician first disconnects the male luer lock component 58 and the female luer lock component 60. Once the male luer lock component 58 is separated from the female luer lock component 60, the physician moves the male luer lock component 58 proximally away from the female luer lock component 58. The movement of the male luer lock component 58 in the proximal direction also causes the wire components 63 to move in the proximal direction. The force created by the movement of the male luer lock component 58 and the wire components 63 releases the side portions 70 of the bottom portion 68 of the top cap 65 to release from the top portion 67. The physician may then move the released side portions 70 of the top cap 65 distally by moving the male luer lock component 58 in the distal direction. The distal movement of the side portions 70 allows the stent 19a to be released and deployed into the patient. The bowed configuration of the wire components 63 allows the released side portions 70 of the bottom portion 68 of the top cap 65 to move radially and axially away from the self-expanding Z-stent 19a. Following the deployment of the self-expanding Z-stent 19a, the male luer lock component 58 is moved distally in the direction of the female luer lock component 60.

Once the endoluminal prosthesis 20 is fully deployed in the targeted vessel, the physician retracts the delivery device 10 from the body of the patient. In order to retract the top cap assembly 34 when it is in the released position, the physician would move the male luer lock component 58 in a proximal direction. The proximal movement of the male luer lock component 58, along with the wire components 63, retracts the released side portions 70 into close proximity with the outer surface of the cannula 15. Preferably, the side portions 70 are brought in close proximity to the outer surface of the cannula 15 in a position distal to the top portion 67 of the top cap 65. The physician would then remove the separated top portion 67 and side portions 68 of the top cap 65 through the lumen of the endoluminal prosthesis 20 through the delivery sheath 30 of the delivery device 10. This emergency release procedure provides the advantage of allowing the physician to deploy the self-expanding Z-stent 19a without causing additional trauma to the patient by the forceful deployment of the attachment stent through pushing and pulling on the delivery device 10 or by converting the endovascular procedure to an open surgery procedure.

Throughout this specification various indications have been given as to preferred and alternative embodiments of the invention. However, the foregoing detailed description is to be regarded as illustrative rather than limiting and the invention is not limited to any one of the provided embodiments. It should be understood that it is the appended claims, including all equivalents, that are intended to define the spirit and scope of this invention.

The invention claimed is:

1. A releasable top cap assembly for a delivery device, comprising:
   a top cap having a top portion and a bottom portion releasably attached to the top portion, the bottom portion comprising two adjacent side portions, the adjacent side portions being separable from one another;
   a cannula disposed through the top cap having a proximal end and a distal end;
   a connector attached to the proximal end of the cannula, and,
   a pair of wire components extending substantially within an interior lumen of the cannula, each wire component having a distal end and a proximal end, the proximal end of each wire component attached to the connector and the distal end of each wire component attached to the side portions of the top cap assembly.

2. The releasable top cap assembly of claim 1, where the connector comprises a male luer lock component and a female luer lock component.

3. The releasable top cap assembly of claim 2, where the pair of wire components is attached to the male luer lock component.

4. The releasable top cap assembly of claim 3, where the two side portions of the top cap are released upon movement of the male luer lock component.

5. The releasable top cap assembly of claim 1, where the distal ends of the pair of wire components are curved outward from an outer surface of the cannula.

6. The releasable top cap assembly of claim 1, where at least two apertures are disposed on opposing sides of the cannula.

7. The releasable top cap assembly of claim 6, where the two apertures are positioned near the distal end of the cannula.

8. The releasable top cap assembly of claim 6, where the two apertures are sized to accommodate the diameter of the wire components.

9. The releasable top cap assembly of claim 1, where the side portions are attached to an outer edge of the top portion.

10. A delivery device for an endoluminal prosthesis, comprising:
    a dilator having a distal end and a proximal end;
    a releasable top cap assembly positioned proximal to the dilator, the releasable top cap assembly comprising
       a top cap having a top portion and a bottom portion releasably attached to the top portion, the bottom portion comprising two adjacent side portions, the adjacent side portions being separable from one another;
       a cannula disposed through the top cap having a proximal end and a distal end;
       a connector attached to the proximal end of the cannula; and,
       a pair of wire components extending substantially within an interior lumen of the cannula, each wire component having a distal end and a proximal end, the proximal end of each wire component attached to the connector and the distal end of each wire component attached to the side portions of the top cap assembly.

11. The delivery device of claim 10, where the connector comprises a male luer lock component and a female luer lock component.

12. The delivery device of claim 10, where the distal ends of the pair of wire components are curved outward from an outer surface of the cannula.

13. The delivery device of claim 10, where at least two apertures are disposed on opposing sides of the cannula.

14. The delivery device of claim 13, where the two apertures are positioned near the distal end of the cannula.

15. The delivery device of claim 13, where the two apertures are sized to accommodate the diameter of the wire components.

16. The delivery device of claim 15, where each wire component is disposed through the opposing apertures in the cannula.

17. The delivery device of claim 10, where the side portions are attached to an outer edge of the top portion.

18. The delivery device of claim 11, where the two side portions of the top cap are released from the top portion upon proximal movement of the male luer lock component.

19. The delivery device of claim 18, where the male luer lock component is moved in a proximal direction to release the two side portions from the top portion of the top cap.

20. A system for endoluminally delivering and deploying an endoluminal prosthesis, comprising:
    a prosthesis having an end portion and a body portion, the end portion including a stent;
    a releasable top cap assembly for maintaining at least a portion of the stent until deployment, the releasable top cap assembly comprising,
       a top cap having a top portion and a bottom portion releasably attached to the top portion, the bottom portion comprising two adjacent side portions, the adjacent side portions being separable from one another;
       a cannula disposed through the top cap having a proximal end and a distal end;
       a connector attached to the proximal end of the cannula; and,
       a pair of wire components extending substantially within an interior lumen of the cannula, each wire component having a distal end and a proximal end,
    where the distal end of each wire component is bowed outwardly in the direction of the side portions of the top cap and where the two side portions of the top cap are released upon movement of a locking mechanism.

* * * * *